US006887961B2

(12) United States Patent
Soerens et al.

(10) Patent No.: US 6,887,961 B2
(45) Date of Patent: May 3, 2005

(54) ABSORBENT BINDER COMPOSITION AND METHOD OF MAKING IT

(75) Inventors: Dave Allen Soerens, Neenah, WI (US); Jason Matthew Laumer, Appleton, WI (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 107 days.

(21) Appl. No.: 10/427,809

(22) Filed: May 1, 2003

(65) Prior Publication Data

US 2004/0019168 A1 Jan. 29, 2004

Related U.S. Application Data

(63) Continuation-in-part of application No. 10/206,883, filed on Jul. 26, 2002, now Pat. No. 6,737,491, which is a continuation-in-part of application No. 10/324,478, filed on Dec. 20, 2002.

(51) Int. Cl.[7] .............................................. C08F 118/00
(52) U.S. Cl. ..................... 526/320; 526/271; 526/277; 526/279; 526/287; 526/317.1; 526/332
(58) Field of Search ................................ 526/271, 277, 526/279, 287, 317.1, 320, 332

(56) References Cited

U.S. PATENT DOCUMENTS

| | | |
|---|---|---|
| 3,617,362 A | 11/1971 | Bemmels et al. |
| 3,951,893 A * | 4/1976 | Gander ..................... 524/322 |
| 3,963,605 A | 6/1976 | Seabourn |
| 4,251,643 A | 2/1981 | Harada et al. |
| 4,291,136 A | 9/1981 | Keogh |
| 4,328,323 A | 5/1982 | Keogh |
| 4,343,917 A | 8/1982 | Keogh |
| 4,353,997 A | 10/1982 | Keogh |
| 4,369,289 A | 1/1983 | Keogh |
| 4,408,011 A | 10/1983 | Barnabeo |
| 4,434,272 A | 2/1984 | Keogh |
| 4,440,907 A | 4/1984 | Keogh |
| 4,446,279 A | 5/1984 | Keogh |
| 4,459,396 A | 7/1984 | Yamasaki et al. |
| 4,489,029 A | 12/1984 | Keogh et al. |
| 4,493,924 A | 1/1985 | Rifi |
| 4,526,930 A | 7/1985 | Keogh |
| 4,551,504 A | 11/1985 | Barnabeo |
| 4,575,535 A | 3/1986 | Keogh |
| 4,579,913 A | 4/1986 | Keogh |
| 4,593,071 A | 6/1986 | Keogh |
| 4,676,820 A | 6/1987 | Le Sergent et al. |
| 4,753,993 A | 6/1988 | Keogh |
| 4,767,820 A | 8/1988 | Keogh |
| 4,921,136 A | 5/1990 | Roggenburg, Jr. |
| 4,940,646 A | 7/1990 | Pawlowski |
| 5,047,476 A | 9/1991 | Keogh |
| 5,089,564 A | 2/1992 | Bullen |
| 5,112,919 A | 5/1992 | Furrer et al. |
| 5,145,906 A | 9/1992 | Chambers et al. |
| 5,196,470 A | 3/1993 | Anderson et al. |
| 5,204,404 A | 4/1993 | Werner, Jr. et al. |
| 5,364,382 A | 11/1994 | Latimer et al. |
| 5,389,728 A | 2/1995 | Prejean |
| 5,532,350 A | 7/1996 | Cottrell et al. |
| 5,656,132 A | 8/1997 | Farrington, Jr. et al. |
| 5,853,867 A | 12/1998 | Harada et al. |
| 5,859,074 A | 1/1999 | Rezai et al. |
| 5,911,937 A | 6/1999 | Hekal |
| 5,932,668 A | 8/1999 | Friebe et al. |
| 5,961,763 A | 10/1999 | Makoui et al. |
| 6,020,171 A | 2/2000 | Saito et al. |
| 6,054,523 A | 4/2000 | Braun et al. |
| 6,110,533 A | 8/2000 | Cote et al. |
| 6,300,275 B1 * | 10/2001 | Weir ......................... 502/405 |
| 6,380,298 B2 | 4/2002 | Flautt et al. |
| 6,403,857 B1 | 6/2002 | Gross et al. |
| 6,417,425 B1 | 7/2002 | Whitmore et al. |
| 6,596,402 B2 | 7/2003 | Soerens et al. |
| 6,689,934 B2 * | 2/2004 | Dodge et al. ............... 604/367 |
| 2002/0090453 A1 | 7/2002 | Muthiah et al. |
| 2003/0149413 A1 | 8/2003 | Mehawej |

FOREIGN PATENT DOCUMENTS

| | | |
|---|---|---|
| CA | 756 190 | 4/1967 |
| EP | 0 132 910 A2 | 2/1985 |
| EP | 0 705 861 A1 | 4/1996 |
| EP | 0 844 265 A1 | 5/1998 |
| EP | 0 992 252 | 4/2000 |
| EP | 1 013 291 A1 | 6/2000 |
| EP | 1 059 320 A2 | 12/2000 |
| EP | 1 199 059 | 4/2002 |
| WO | 99/57201 | 11/1999 |
| WO | WO 02/053664 A2 | 7/2002 |

* cited by examiner

*Primary Examiner*—Helen L. Pezzuto
(74) *Attorney, Agent, or Firm*—Pauley Petersen & Erickson

(57) ABSTRACT

An absorbent binder composition is provided which is capable of crosslinking after application to a substrate, in the absence of radiation, at a temperature of about 120° C. or less. The absorbent binder composition includes about 15 to about 99.8% by mass monoethylenically unsaturated polymer units, about 0.1 to about 20% by mass polyacrylate ester units having an alkoxysilane functionality, and about 0.1 to about 75% by mass of polymer units selected from polyolefin glycols and polyolefin oxides. The absorbent binder composition can be prepared using a template polymerization process, with the preformed polyolefin glycol or polyolefin oxide serving as a template polymer.

28 Claims, No Drawings

ABSORBENT BINDER COMPOSITION AND METHOD OF MAKING IT

RELATED APPLICATIONS

This application is a continuation-in-part of U.S. patent application Ser. No. 10/206,883, filed on 26 Jul. 2002, U.S. Pat. No. 6,737,491 the disclosure of which is incorporated by reference. This application is also a continuation-in-part of U.S. patent application Ser. No. 10/324,478, filed 20 Dec. 2002, pending disclosure of which is incorporated by reference.

BACKGROUND OF THE INVENTION

This invention is directed to an absorbent binder or coating composition, and a method of making the absorbent binder or coating composition.

Adhesives, or binders, are a necessary element of many absorbent products. While adhesives beneficially hold products together, adhesives may also have a tendency to interfere with the absorbency of fluids in absorbent products. Adhesives are typically hydrophobic and therefore are not conducive to absorbency or liquid transfer functions. Furthermore, most adhesives are non-absorbent and thus serve no liquid retention function.

Hydrophilic adhesives are known, such as adhesives formulated from water-soluble polymers such as poly(vinyl alcohol), poly(vinyl methyl ether), poly(vinyl pyrrolidone), poly(ethylene oxide), or cellulose derivatives such as hydroxypropyl cellulose. Dextrans, starches and vegetable gums have been used to provide hydrophilic adhesives. These materials provide adhesion under dry conditions. However, upon exposure to aqueous fluids, these materials lose bonding capability because they are substantially soluble in aqueous fluids.

A known approach for making hydrophilic adhesives more functional upon exposure to aqueous fluid is to crosslink the water-soluble polymers. As a result of crosslinking, the material becomes swellable, and no longer soluble, in aqueous fluid. However, crosslinked polymers are difficult to apply to substrates or to establish intimate contact with surfaces because the crosslinked polymers are solid materials and have little or no ability to flow. Some of the crosslinked materials are fairly stiff, and inhibit the flexibility of the absorbent product.

What is therefore needed is a hydrophilic binder or coating that has latent crosslinking capability and which can be produced at attractive cost. Such binder or coating could be easily applied, like a water-soluble polymer, since the hydrophilic binder or coating would be capable of flow prior to crosslinking. Latent crosslinking capability would also provide a simple means of crosslinking the polymer after the polymer has established intimate contact with substrates or has formed a desired final shape or form. There is also a need or desire for such a binder which has a high level of flexibility.

Post-application crosslinking techniques are well known. Typical means of inducing the formation of crosslinks include high temperature "curing" or exposure to radiation, such as ultraviolet or gamma radiation. Another known means of post-application crosslinking is moisture-induced crosslinking.

Recent development efforts have provided coating materials for a variety of uses. For example, U.S. Pat. No. 6,054,523, to Braun et al., describes materials that are formed from organopolysiloxanes containing groups that are capable of condensation, a condensation catalyst, an organopolysiloxane resin, a compound containing a basic nitrogen, and polyvinyl alcohol. The materials are reported to be suitable for use as hydrophobic coatings and for paints and sealing compositions.

Anderson et al., in U.S. Pat. No. 5,196,470, reported an alcohol-based, water-soluble binder composition. Because this composition is water-soluble and not cross-linked, it has no absorbency.

Others have reported the production of graft copolymers having silane functional groups that permitted the initiation of cross-linking by exposure to moisture. Prejean (U.S. Pat. No. 5,389,728) describes a melt-processable, moisture-curable graft copolymer that was the reaction product of ethylene, a 1–8 carbon alkyl acrylate or methacrylate, a glycidyl containing monomer such as glycidyl acrylate or methacrylate, onto which has been grafted N-tert-butylaminopropyl trimethoxysilane. The resulting copolymers were reported to be usefull as adhesives and for wire and cable coatings.

Furrer et al., in U.S. Pat. No. 5,112,919, reported a moisture-crosslinkable polymer that was produced by blending a thermoplastic base polymer, such as polyethylene, or a copolymer of ethylene, with 1-butene, 1-hexene, 1-octene, or the like; a solid carrier polymer, such as ethylene vinylacetate copolymer (EVA), containing a silane, such as vinyltrimethoxysilane; and a free-radical generator, such as an organic peroxide; and heating the mixture. The copolymers could then be cross-linked by reaction in the presence of water and a catalyst, such as dibutyltin dilaurate, or stannous octoate.

U.S. Pat. No. 4,593,071 to Keough reported moisture cross-linkable ethylene copolymers having pendant silane acryloxy groups. The resultant cross-linked polymers were reported to be especially resistant to moisture and to be useful for extruded coatings around wires and cables. The same group has reported similar moisture curable polymers involving silanes in U.S. Pat. Nos. 5,047,476, 4,767,820, 4,753,993, 4,579,913, 4,575,535, 4,551,504, 4,526,930, 4,493,924, 4,489,029, 4,446,279, 4,440,907, 4,434,272, 4,408,011, 4,369,289, 4,353,997, 4,343,917, 4,328,323, and 4,291,136.

U.S. Pat. No. 5,204,404 to Werner reported crosslinkable hydrophobic acrylate ester copolymers including 0.1 to 10% acrylic acid. The resultant cross-linked polymers were reported to be useful for painting and refinishing the exterior of automobiles.

These examples of moisture-induced crosslinking are applied to substantially hydrophobic polymers. Since the cured products of these formulations are reported to be useful for coverings for wire and cable, and for non-conductive coatings for electrical conductors, and for painting and refinishing the exterior of automobiles, it would be expected that they are durable coatings for which properties such as water absorbency would be a disadvantage.

There is thus a need within the field of absorbent products for absorbent binders, adhesives, or coatings. Furthermore, there is a need within the field of absorbent products for such absorbent binders, adhesives, or coatings that can be prepared by post-application, moisture-induced crosslinking of hydrophilic polymers, at a reasonable cost, which have a high level of flexibility.

SUMMARY OF THE INVENTION

The present invention is directed to an improved absorbent binder composition and method of making it. The absorbent binder composition includes a hydrophilic polymer which is capable of post-application, moisture-induced crosslinking, is relatively inexpensive to produce, and has a high level of flexibility. The flexible nature of the absorbent binder is useful when the binder is employed in personal care absorbent articles, as well as in other products which must be flexible and/or conformable to the wearer's body.

The absorbent binder composition includes about 15 to about 99.8% by mass of monoethylenically unsaturated polymer units. Suitable monoethylenically unsaturated polymers include without limitation carboxylic acid, sulphonic acid, phosphonic acid, and salts of the foregoing. The absorbent binder composition also includes about 0.1 to about 20% by mass of acrylate or methacrylate ester units that include an alkoxysilane functionality. Upon exposure to water, the alkoxysilane functionality forms a silanol group which condenses to form a crosslinked polymer.

The absorbent binder composition also includes about 0.1 to about 75% by mass of polyolefin glycol and/or polyolefin oxide units. The polyolefin glycol and/or oxide may include an alpha-olefin having about 2 to about 4 carbon atoms, and may include about 30 to about 15,000 olefin glycol and/or oxide units per molecule. The polyolefin glycol and/or oxide may be graft polymerized with the acrylate or methacrylate ester to form a graft copolymer. The polyolefin glycol and/or oxide may be a homopolymer or copolymer. The polyolefin glycol and/or oxide may be a block copolymer including olefin glycol or oxide units having different numbers of carbon atoms, for instance, block copolymers of ethylene oxide and propylene oxide. The polyolefin glycol and/or oxide provides the absorbent binder composition with enhanced flexibility. Thus, the absorbent binder composition has enhanced adhesion in a wet condition, absorbency, and flexibility.

The absorbent binder composition may be used in the manufacture of absorbent products, and therefore may be applied to such substrates as nonwoven webs, woven webs, knitted fabrics, cellulose tissue, plastic film, stranded composites, staple fibers, yarns, elastomer net composites, or any other suitable substrates. Examples of suitable types of plastic film substrates include those made of polypropylene, low density polyethylene, high density polyethylene, linear low density polyethylene, and ultra low density polyethylene. Examples of absorbent articles in which the absorbent binder composition may be used include diapers, diaper pants, training pants, feminine hygiene products, incontinence products, swimwear garments, and the like.

The absorbent binder composition can be prepared using a template polymerization process by which the monoethylenically unsaturated polymer and acrylate or methacrylate ester are polymerized in the presence of a pre-formed template polymer, which is the polyolefin glycol and/or polyolefin oxide. The polymerization can be carried out by reacting two different monoethylenically unsaturated monomers, one of which contains an alkoxysilane functionality. The polymerization may be induced by heat, radiation, redox chemical reactions, and other techniques. Suitable radiation initiators include without limitation ultraviolet, microwave, and electron beam radiation. The initiator generates free radicals to cause copolymerization of the monomers. In one embodiment, the polymerization reaction is carried out in an organic solvent such as ethanol. The polymerization may also occur in an aqueous solution, or in a combined aqueous and organic solvent.

The polyolefin glycol and/or oxide may or may not be graft polymerized onto the acrylate or methacrylate units during the polymerization process. The resulting absorbent binder composition may contain the polyolefin glycol and/or oxide as a separate component, or as part of the copolymer, or a combination of both.

The resulting polymer has latent moisture-induced crosslinking capability due to the alkoxysilane functionality. This polymer may be applied, in a flowable state, to a substrate or other end use application. Moisture-induced crosslinking may be accomplished through hydrolysis of the alkoxysilane and subsequent condensation upon removal of the solvent from the substrate, either by evaporation of the solvent from the substrate or using any other effective technique. Alternatively, the hydrolysis of the alkoxysilane and subsequent condensation may occur after solvent removal by exposure of the coating to moisture in ambient air.

With the foregoing in mind, it is a feature and advantage of the invention to provide an absorbent binder composition and method of making it.

DEFINITIONS

Within the context of this specification, each term or phrase below will include the following meaning or meanings.

"Binder" includes materials which are capable of attaching themselves to a substrate or are capable of attaching other substances to a substrate.

"Feminine hygiene products" include sanitary pads and napkins, as well as tampons and interlabial feminine hygiene products.

"Fluid" refers to a substance in the form of a liquid or gas at room temperature and atmospheric pressure.

"High density polyethylene (HDPE)" refers to a polyethylene having a density of about 0.95 $g/cm^3$ or greater.

"Knife over roll coating" refers to a process in which a knife is positioned, with a specified gap, above a substrate that is moving beneath the knife on a moving roll. In this manner, the knife spreads a specified thickness of coating material onto the substrate.

"Layer" when used in the singular can have the dual meaning of a single element or a plurality of elements.

"Linear low density polyethylene (LLDPE)" refers to polymers of ethylene and higher alpha-olefin comonomers such as $C_3$–$C_{12}$ comonomers, and combinations thereof, having a density of about 0.900 to about 0.935 $g/cm^3$.

"Low density polyethylene (LDPE)" refers to a polyethylene having a density between about 0.91 and about 0.925 $g/cm^3$.

"Modifying agent" refers to a substance that may be added to a composition to modify the physical properties of the composition, such as the color or texture of the composition.

"Nonwoven" or "nonwoven web" refers to materials and webs or material having a structure of fibers or filaments which are interlaid, but not in an identifiable manner as in a knitted fabric. The terms "fiber" and "filament" are used interchangeably. Nonwoven fabrics or webs have been formed from many processes such as, for example, meltblowing processes, spunbonding processes, air laying processes, and bonded carded web processes. The basis weight of nonwoven fabrics is usually expressed in ounces of material per square yard (osy) or grams per square meter (gsm) and the fiber diameters are usually expressed in microns. (Note that to convert from osy to gsm, multiply osy by 33.91.)

"Personal care absorbent product" includes diapers, diaper pants, training pants, swim wear, absorbent underpants, adult incontinence products, feminine hygiene products, and the like.

"Roll printing" or "roll coating" refers to a process in which the application of a deposited material, generally as a paste, onto a substrate is carried out by transferring the deposited material from a roll onto the substrate in a more or less uniform layer using one or more rolls, which may be engraved, and a pool cylinder. A doctor blade is used to scrape any excess deposited material from the rolls or substrate. The doctor blade may be flat or have a patterned edge such as slots or ridges.

"Rotary screen printing" or "rotary screen coating" refers to a process that is a combination of roll printing or coating and screen printing or coating.

"Screen printing" or "screen coating" refers to a method of applying a deposited material by forcing the material to be deposited through a screen that may have uniform openings or patterned openings.

"Stranded composites" refer to sheets of material to which strands of an elastomeric material are adhered to create an elastomeric composite.

"Superabsorbent" refers to a water-swellable, water-insoluble organic or inorganic material capable, under the most favorable conditions, of absorbing at least about 10 times its weight and, more desirably, at least about 25 times its weight in an aqueous solution containing 0.9 weight percent sodium chloride, The superabsorbent materials can be natural, synthetic, and modified natural polymers and materials. In addition, the superabsorbent materials can be inorganic materials, such as silica gels, or organic compounds such as cross-linked polymers. A material is "absorbent" if it absorbs at least five times its weight of the aqueous solution under these conditions.

"Unit" or "polymer unit" refers to a monomer or polymer portion of a copolymer molecule or blend component that includes a different molecular structure, compared to another portion of the copolymer or blend.

DESCRIPTION OF PREFERRED EMBODIMENTS

The present invention is directed to an absorbent binder composition that includes a flexible hydrophilic polymer having the capability of post-application, moisture-induced crosslinking. The present invention also includes a method of making and applying such an absorbent binder composition. The absorbent binder composition can provide fluid retention properties in addition to adhesive properties and flexibility. Thus, the absorbent binder composition is particularly suitable for use in forming absorbent products.

The absorbent binder composition includes about 15 to about 99.8% by mass of monoethylenically unsaturated polymer units, suitably about 25 to about 89.5% by mass, particularly about 30 to about 79% by mass, or about 50 to about 70% by mass. Suitable monoethylenically unsaturated polymer units include without limitation monoethylenically unsaturated carboxylic acid units and salts thereof, monoethylenically unsaturated sulphonic acid units and salts thereof, and monoethylenically unsaturated phosphonic acid units and salts thereof. Suitable monoethylenically unsaturated monomers that can be used to form the monoethylenically unsaturated polymer units include without limitation:

a) Carboxyl group-containing monomers including monoethylenically unsaturated mono or poly-carboxylic acids, such as (meth)acrylic acid (meaning acrylic acid or methacrylic acid; similar notations are used hereinafter), maleic acid, fumaric acid, crotonic acid, sorbic acid, itaconic acid, and cinnamic acid;

b) Carboxylic acid anhydride group-containing monomers, including monoethylenically unsaturated polycarboxylic acid anhydrides (such as maleic anhydride);

c) Carboxylic acid salt group-containing monomers including water-soluble salts (alkali metal salts, ammonium salts, amine salts, etc.) of monoethylenically unsaturated mono- or poly-carboxylic acids (such as sodium (meth)acrylate, trimethylamine (meth)acrylate, triethanolamine (meth)acrylate), sodium maleate, methylamine maleate;

d) Sulfonic acid group-containing monomers, including aliphatic or aromatic vinyl sulfonic acids (such as vinylsulfonic acid, allyl sulfonic acid, vinyltoluenesulfonic acid, stryrene sulfonic acid), (meth)acrylic sulfonic acids [such as sulfopropyl (meth)acrylate, 2-hydroxy-3-(meth)acryloxy propyl sulfonic acid];

e) Sulfonic acid salt group-containing monomers, including alkali metal salts, ammonium salts, amine salts of sulfonic acid group containing monomers as mentioned above; and/or f) Amide group-containing monomers, including vinylformamide, (meth)acrylamide, N-alkyl (meth)acrylamides (such as N-methylacrylamide, N-hexylacrylamide), N,N-dialkyl (meth)acryl amides (such as N,N-dimethylacrylamide, N,N-di-n-propylacrylamide), N-hydroxyalkyl (meth)acrylamides [such as N-methylol (meth)acrylamide, N-hydroxyethyl (meth)acrylamide], N,N-dihydroxyalkyl (meth)acrylamides [such as N,N-dihydroxyethyl (meth)acrylamide], 3-acrylamidopropyl trimethyl ammonium chloride, vinyl lactams (such as N-vinylpyrrolidone).

The absorbent binder composition also includes about 0.1 to about 20% by mass of polyacrylate ester units, such as acrylate and/or methacrylate ester units, that include an alkoxysilane functionality. The acrylate and/or methacrylate ester units are copolymerized with the monoethylenically unsaturated monomer units. In particular, the absorbent binder composition may include about 0.5 to about 15% by mass of the acrylate and/or methacrylate ester units, for instance about 1.0 to about 10% by mass, for instance about 1.5 to about 5.5% by mass.

The alkoxysilane functionality is a functional group or moiety that reacts with water to form a silanol group. One suitable alkoxysilane group is a trialkoxy silane group having the following structure:

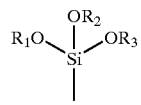

wherein $R_1$, $R_2$ and $R_3$ are alkyl groups independently having from 1 to 6 carbon atoms.

The term "monomer(s)" as used herein includes monomers, oligomers, polymers, mixtures of monomers, oligomers and/or polymers, and any other reactive chemical species which is capable of co-polymerization with monoethylenically unsaturated carboxylic, sulphonic or phosphoric acid or salts thereof. Ethylenically unsaturated monomers containing a trialkoxy silane functional group are appropriate for this invention and are desired. Suitable ethylenically unsaturated monomers include acrylates and methacrylates. A particularly ethylenically unsaturated monomer containing a trialkoxy silane functional group is methacryloxypropyl trimethoxy silane, commercially available from Dow Corning, having offices in Midland, Mich., under the trade designation Z-6030 Silane. Other suitable ethylenically unsaturated monomers containing a trialkoxy silane functional group include, but are not limited to, methacryloxyethyl trimethoxy silane, methacryloxypropyl triethoxy silane, methacryloxypropyl tripropoxy silane, acryloxypropylmethyl dimethoxy silane, 3-acryloxypropyl trimethoxy silane, 3-methacryloxypropylmethyl diethoxy silane, 3-methacryloxypropylmethyl dimethoxy silane, and 3-methacryloxypropyl tris(methoxyethoxy)silane. However, it is contemplated that a wide range of vinyl and acrylic monomers having trialkoxy silane functional groups or a moiety that reacts easily with water to form a silanol group, such as a chlorosilane or an acetoxysilane, provide the desired effects are effective monomers for copolymerization in accordance with the present invention.

In addition to monomers capable of co-polymerization that contain a trialkoxy silane functional group, it is also feasible to use a monomer capable of copolymerization that can subsequently be reacted with a compound containing a trialkoxy silane functional group or a moiety that reacts with water to form a silanol group. Such a monomer may contain, but is not limited to, an amine or an alcohol. An amine group incorporated into the co-polymer may subsequently be reacted with, for example, but not limited to, (3-chloropropyl)trimethoxysilane. An alcohol group incorporated into the copolymer may subsequently be reacted with, for example, but not limited to, tetramethoxysilane.

The absorbent binder composition also includes about 0.1 to about 75% by mass polyolefin glycol and/or polyolefin oxide units, suitably about 5 to about 75% by mass, particularly about 10 to about 60% by mass, particularly about 20 to about 50% by mass, particularly about 30 to about 40% by mass. The polyolefin glycol or oxide may be a glycol or oxide of an olefin polymer having about 2 to about 4 carbon atoms. Polyethylene glycol, polyethylene oxide, polypropylene glycol and polypropylene oxide are examples of suitable polymer units. The polyolefin glycol and/or polyolefin oxide may include on average about 30 to about 15,000 glycol and/or oxide units per molecule. The weight average molecular weight of polyolefin glycol units may range from about 200 to about 8000. When polyolefin oxide units are employed, they may have a weight average molecular weight of about 100,000 to about 600,000.

Polyolefin glycols and polyolefin oxides are commercially available, and are common. To prepare the absorbent binder composition of the invention, a pre-formed polyolefin glycol and/or oxide may be dissolved or dispersed in a reaction vessel which includes an aqueous solvent or carrier, an organic solvent or carrier such as ethanol, or a miscible combination of aqueous and organic solvent or carrier. The monomers used to form the monoethylenically unsaturated polymer units and the polyacrylate ester units are added to the solution and polymerized using a template polymerization process in which the polyolefin glycol or oxide serves as a template polymer. Before initiation, the polar groups of the monomers, for instance the acid groups of acrylic acid, are attracted to the polyolefin glycol and/or polyolefin oxide through hydrogen bonding. The steric alignment of the monomers, with the polyolefin glycol and/or oxide serving as backbone, aids in the polymerization and typically increases the chain length of the polymerizing unit. During the polymerization, radical polymerizing chains may become attached to the template polymer, resulting in grafting of polyolefin glycol and/or oxide to the copolymer being formed. However, this graft polymerization need not occur. The resulting absorbent binder composition includes the polyolefin glycol and/or oxide attached to, and/or blended with, the copolymer of the monoethylenically unsaturated polymer units and the acrylate or methacrylate ester units that include the alkoxysilane functionality.

The polymerization may be initiated using a variety of methods, including without limitation thermal energy, ultraviolet light, and redox chemical reactions. A solution of the above ingredients may be added to an initiator solution at a temperature suitable for generating free radicals, for instance about 50 to about 90° C. An initiator may be prepared by dissolving an initiator in an organic or aqueous solvent. A suitable class of initiators are organic peroxides and azo compounds, with benzoyl peroxide and azobisisobutylnitrile (ABN) as examples.

Compounds containing an O—O, S—S, or N=N bond may be used as thermal initiators. Compounds containing O—O bonds; i.e., peroxides, are commonly used as initiators for polymerization. Such commonly used peroxide initiators include: alkyl, dialkyl, diaryl and arylalkyl peroxides such as cumyl peroxide, t-butyl peroxide, di-t-butyl peroxide, dicumyl peroxide, cumyl butyl peroxide, 1,1-di-t-butyl peroxy-3,5,5-trimethylcyclohexane, 2,5-dimethyl-2,5-di(t-butylperoxy)hexane, 2,5-dimethyl-2,5-bis(t-butylperoxy)hexyne-3 and bis(a-t-butyl peroxyisopropylbenzene); acyl peroxides such as acetyl peroxides and benzoyl peroxides; hydroperoxides such as cumyl hydroperoxide, t-butyl hydroperoxide, p-methane hydroperoxide, pinane hydroperoxide and cumene hydroperoxide; peresters or peroxyosters such as t-butyl peroxypivalate, t-butyl peroctoate, t butyl perbenzoate, 2,5-dimethylhexyl-2,5-di(perbenzoate) and t-butyl di(perphthalate); alkylsulfonyl peroxides; dialkyl peroxymonocarbonates; dialkyl peroxydicarbonates; diperoxyketals; ketone peroxides such as cyclohexanone peroxide and methyl ethyl ketone peroxide. Additionally, azo compounds such as 2,2'-azobisisobutyronitrile abbreviated as AIBN, 2,2'-azobis(2,4-dimethylpentanenitrile) and 1,1'-azobis (cyclohexanecarbonitrile) may be used as the initiator.

Alternatively, redox initiation can be used for the polymerization. This method incorporates a first monomer solution that includes a reducing polymerization initiator. Suitable reducing polymerization initiators include, but are not limited to, ascorbic acid, alkali metal sulfites, alkali metal bisulfites, ammonium sulfite, ammonium bisulfite, alkali metal hydrogen sulfites, ferrous metal salts such as ferrous sulfates, sugars, aldehydes, primary and secondary alcohols, and combinations thereof. In one embodiment, the reducing polymerization initiator includes ascorbic acid.

The second monomer solution further includes an oxidizing polymerization initiator. Suitable oxidizing initiators include, but are not limited to, hydrogen peroxide, alkali metal persulfates, ammonium persulfate, alkylhydroperoxides, peresters, diacryl peroxides, silver salts, and combinations thereof. In one embodiment, the oxidizing polymerization initiator includes hydrogen peroxide.

Generally, when the first aqueous monomer solution is combined with the second aqueous monomer solution the reducing polymerization initiator reacts with the oxidizing polymerization initiator, e.g., a redox reaction, thereby initiating a polymerization reaction to form a binder composition including a monoethylenically unsaturated monomer and an ethylenically unsaturated monomer that has post-application, moisture-induced crosslinking capability.

In one embodiment, the monoethylenically unsaturated polymer unit is a cationic polymer. The cationic polymer is advantageous because it provides a) inherent antimicrobial properties, b) enhanced attraction and retention into cellulose fibers in a suspension, and c) enhanced attraction to superabsorbent particles which are negatively charged. Suitable cationic polymers include those prepared by copolymerizing a monomer 1) selected from a) acryloyloxyethyl-trialkyl-substituted ammonium salts, b) acryloyloxypropyl-trialkyl-substituted ammonium salts, c) acrylamidoethyl-trialkyl-substituted ammonium salts, and d) acrylamidopropyl-trialkyl-substituted ammonium salts, with a monomer 2) selected from a) methacryl esters which contain an alkoxysilane group capable of moisture-induced crosslinking and b) acryl esters which contain an alkoxysilane group capable of moisture-induced crosslinking. Other monomers may also be present, for instance, an acrylic acid or acrylamide. The polymerization is conducted in the presence of a polyolefin glycol and/or polyolefin oxide as described above, suitably a polyethylene glycol. The cationic monoethylenically unsaturated monomer unit and the polyolefin glycol are present in the amounts described above.

The cationic monoethylenically unsaturated polymer may be prepared by a redox initiation process, according to the following reaction. The cationic copolymer is then coated and dried onto a substrate to form the crosslinked absorbent coating.

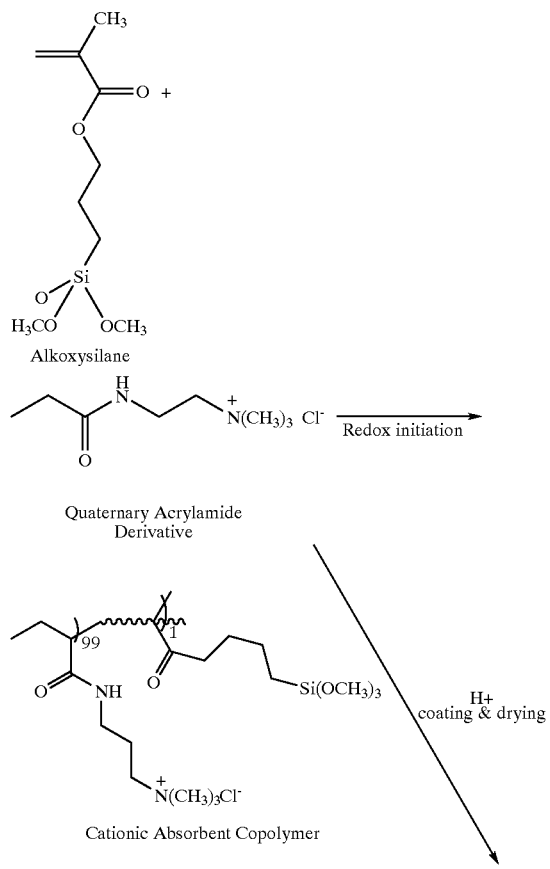

Alkoxysilane

Quaternary Acrylamide Derivative

Cationic Absorbent Copolymer

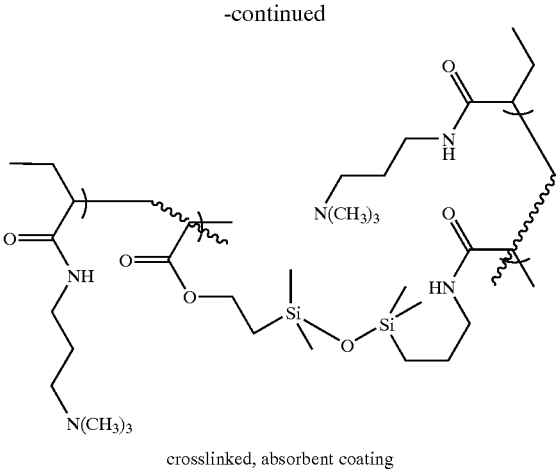

crosslinked, absorbent coating

Applications where the cationic absorbent binder composition is useful include without limitation fabric and foam coatings for gauze and wound dressings. The cationic absorbent binder composition adheres to the substrate and wound, and helps contain antimicrobial and healing agents. The cationic absorbent binder composition may also form a lubricious, antimicrobial coating for a catheter or guide wire. Additionally, the cationic absorbent binder composition may be used to coat cellulose tissue or paper in a wide variety of applications ranging from absorbent paper towels to cartons for carrying hot food. The cationic absorbent binder composition may also be provided in a spray or roll-on form for use as a deodorant.

In one embodiment, the absorbent binder composition is made by combining a first aqueous monomer solution including a reducing polymerization initiator with a second aqueous monomer solution including an oxidizing polymerization initiator, wherein the initiators react to form a binder composition. The first aqueous monomer solution further includes a monoethylenically unsaturated monomer and an ethylenically unsaturated monomer that contains an alkoxysilane functionality. The second aqueous monomer solution includes a monoethylenically unsaturated monomer. One or both solutions may include the polyolefin glycol and/or polyolefin oxide template polymer. Suitably, the absorbent binder composition is formed in about 100 minutes or less, or about 60 minutes or less, desirably in about 30 minutes or less, or about 15 minutes or less, or 20 about 10 minutes or less.

The pH of the first and/or second aqueous monomer solution is adjusted to about 4.5 to about 8, suitably about 5.5 to about 7.0. The pH of the first aqueous solution may be adjusted prior to the addition of the ethylenically unsaturated monomer. Desirably, the pH of the first aqueous monomer solution is adjusted prior to the addition of the reducing polymerization initiator. The pH of the second aqueous solution may be adjusted prior to the addition of the oxidizing polymerization initiator. Alternatively, the pH of the combined first and second aqueous monomer solutions may be adjusted to about 4.5 to about 8, suitably about 5.5 to about 7.0.

The amounts of the polymerization ingredients added to the first and second aqueous solutions are selected so as to produce the absorbent binder composition having the composition described above. In one embodiment, a surfactant may be added to the first and/or second aqueous monomer solution to disperse the ethylenically unsaturated monomer.

The first aqueous monomer solution further includes a reducing polymerization initiator. Suitable reducing polymerization initiators include, but are not limited to, ascorbic acid, alkali metal sulfites, alkali metal bisulfites, ammonium sulfite, ammonium bisulfite, alkali metal hydrogen sulfite, ferrous metal salts such as ferrous sulfates, sugars, aldehydes, primary and secondary alcohols, and combinations thereof. In one embodiment, the reducing polymerization initiator includes ascorbic acid.

The second aqueous monomer solution further includes an oxidizing polymerization initiator. Suitable oxidizing initiators include, but are not limited to, hydrogen peroxide, alkali metal persulfates, ammonium persulfate, alkylhydroperoxides, peresters, diacryl peroxides, silver salts, and combinations thereof. In one embodiment, the oxidizing polymerization initiator includes hydrogen peroxide.

Generally, when the first aqueous monomer solution is combined with the second aqueous monomer solution the reducing polymerization initiator reacts with the oxidizing polymerization initiator, e.g. a redox reaction, thereby initiating a polymerization reaction to form a binder composition including a monoethylenically unsaturated monomer and an ethylenically unsaturated monomer that has post-application, moisture-induced crosslinking capability.

The absorbent binder composition may be applied to a substrate and subsequently dried to form a cast film. Once the absorbent binder composition is applied to the substrate, crosslinking can be moisture-induced by hydrolysis and condensation of alkoxysilanes. For example, crosslinking of the absorbent binder composition can be induced by concentrating the absorbent binder composition on the substrate through the removal of the water to promote condensation of silanols generated by hydrolysis of alkoxysilanes. Typically, crosslinking begins at a solution concentration of about 30 percent or greater by weight absorbent binder composition. Furthermore, if the substrate material has hydroxyl group functionality on its surface, then the silanols within the binder composition may react with the hydroxyl groups to form a covalent bond between the binder and the hydroxyl-containing surface. Non-limiting examples of substrates with hydroxyl surface functionality include glass, sand and cellulose.

Alternatively, the absorbent binder composition may be applied to a substrate, such as for the purpose of adhering various components of an absorbent article to one another during the manufacturing process of absorbent articles. Absorbent articles include without limitation diapers, training pants, feminine hygiene articles, adult incontinence garments, medical absorbent articles and the like. In another embodiment, the absorbent binder composition may be applied to a substrate as a coating by itself, thereby serving as an absorbency additive. In either of these embodiments, the absorbent binder composition is suitably present in any concentration that provides a viscosity suitable for the application process. The absorbent binder composition may be applied to the substrate using any suitable application process, including knife over roll coating, or roll coating, either in a continuous coverage or a patterned coverage. Printing applications are other suitable application techniques, including gravure printing, screen, and jet printing. The binder composition may also be applied to the substrate using a spray application.

In another embodiment, the absorbent binder composition may be prepared using a continuous process wherein the polymerization and/or neutralization reaction is carried out in a suitable reactor that conveys the resulting absorbent binder composition, upon completion of the polymerization reaction, directly to an apparatus for applying the absorbent binder composition onto the substrate. Such a continuous process may be desirable where conditions, such as high heat, may cause premature crosslinking of the absorbent binder composition that would hinder application of the absorbent binder composition onto the substrate.

One advantage of the absorbent binder composition of the invention is that it provides a water-soluble ionic polymer capable of sufficient spontaneous crosslinking within about 10 minutes, at a temperature of about 120° C. or less, to reach an absorbent capacity of at least one gram of fluid per gram of absorbent binder composition, suitably at least three grams of fluid per gram of absorbent binder composition, using the centrifuge retention capacity test described herein. The term "spontaneous" crosslinking refers to crosslinking which occurs without radiation, catalysis, or any other inducement other than the specified temperature of about 120° C. or less, suitably about 100° C. or less. Eliminating the need for radiative crosslinking provides a significant processing advantage. The crosslinking at temperatures of about 120° C. or less, suitably about 100° C. or less, permits the absorbent binder composition to be applied to a substrate such as an absorbent article, and then crosslinked without degrading or damaging the substrate. The crosslinking occurs within about 10 minutes, suitably within about 8 minutes, particularly within about 6 minutes provides an efficient, commercially feasible, cost-effective crosslinking process. The ionic polymer may bear a positive charge, a negative charge, or a combination of both, and should have an ionic unit content of about 15 mole percent or greater. The ionic polymer may include a variety of monomer units described above, and suitably contains a carboxyl group-containing unit or a quaternary ammonium-containing unit.

EXAMPLE 1

Two monomer solutions were prepared separately. Solution No. 1 was prepared as follows. To 14.4 grams (0.20 moles) of acrylic acid in a 200 ml beaker was added 33.3 grams of a 18% aqueous solution of polyethylene glycol 8000, followed by a solution of 3.2 grams of sodium hydroxide in 21.4 grams of distilled water. Then, 0.18 grams ($1.02 \times 10^{-3}$ moles) of ascorbic acid was added to the solution. This mixture was stirred with a magnetic stir bar at about 60 rpm in a bath of water at about 23° C. until the ascorbic acid was dissolved and the mixture cooled to 23° C.

Solution No. 2 was prepared in the following manner. To 14.4 grams (0.20 moles) of acrylic acid, in a 300 ml beaker was added to 33.3 grams of a 18% aqueous solution of polyethylene glycol 8000 (mol. wt.=8000) followed by a solution of 3.2 grams of sodium hydroxide in 21.4 grams of distilled water, 0.57 ml of 30% aqueous hydrogen peroxide and 1.0 ml ($5.42 \times 10^{-3}$ moles) of 3-(trimethoxysilyl)propyl methacrylate. The ingredients were added with stirring to produce a clear solution. This mixture was stirred with a magnetic stir bar at about 60 rpm in a bath of water at about 23° C. to provide a clear solution cooled to 23° C.

A third solution was prepared by dissolving 8 grams (0.20 moles) sodium hydroxide in 160 grams of distilled water.

Solution No. 2 was added to Solution No. 1 while stirring with a magnetic stir bar at about 60 rpm. A thermocouple was used to monitor the temperature and observe the reaction exotherm. The polymerization reaction began within about 30 seconds of mixing as the temperature rose from 23° C. to 40° C. A maximum temperature of about 70° C. was observed after three minutes of mixing the two solutions. The polymerization transformed the combined solutions into a soft gel. The gel was cut into pieces of about 1 cm³ and added to the solution of 8 grams (0.20 moles) sodium hydroxide in 160 grams of distilled water. With continued stirring, aided by an Ultraturax homogenizer at 11,000 rpm, the soft gel became a viscous translucent solution.

The resulting aqueous binder composition was cast into a film by pouring 25.1 grams of solution into a polystyrene weigh boat, available from VWR International, catalog no. 12577-027, with surface area of about 80 cm², and allowing the water to evaporate overnight in a hood at room temperature. The resulting film weighed 4.62 grams, indicating a solution concentration of about 18.4%.

The absorbent capacity of the film was tested using the Centrifuge Retention Capacity test described in the test method section. The film had an absorbent capacity of 12.2 g/g.

EXAMPLE 2

An aqueous binder composition was prepared according to the procedure of EXAMPLE 1. This example was used to determine the speed of crosslinking in the following manner. Six 10-cm by 10-cm pieces of loft bonded carded web surge material made according to U.S. Pat. No. 5,364,382, by Kimberly-Clark Corporation, with a basis weight of about 45 gsm and a density of 0.04 g/cm³ measured at a pressure of 0.05 psi, were each immersed in about 12 grams of the binder solution to thoroughly saturate the fabric. The dry weight of each fabric was weighed prior to saturation with the binder solution. The weights of the starting solution and of the residual solution were measured, with the difference being equal to the weight of solution applied to each piece of fabric. The saturated surge sample was placed on an aluminum screen and dried for times ranging from 5 to 15 minutes at 105° C. in a Mathis through-air-dryer oven, available from Werner Mathis in Palmer, Pa. After drying, for the specified time, listed in Table 1, the coated fabric was weighed. After removal from the through-air-dryer oven the absorbent capacity of each of the test fabrics was determined using the Centrifuge Retention Test. The samples were then dried for 3 hours at 80° C. in a Constant Temperature Oven, Model DK-63, available from Scientific Products. The re-dried weight was used to determine the fraction of the binder solution that was extractable. For instance, 100% extractable would be indicative of a fully soluble polymer with no crosslinking and no absorbent capacity. The extent of crosslinking is inversely proportional to the percent of extractable components.

These results (shown in Table 1) indicate crosslinking begins even before the coated fabric is fully dry. While not wishing to be bound by theory, the rate of crosslinking is believed to be a function of the concentration of the polymer in solution. Any means of rapidly removing the solvent, such as higher temperature, greater airflow, or lower pressure, will increase the polymer concentration and the rate of crosslinking.

The percent extractable was calculated as:

$$100\% \times \frac{\text{(weight after drying minus weight after redrying)}}{\text{weight after drying}}$$

EXAMPLE 3

This example relates to the preparation of a cationic absorbent polymer. Two monomer solutions were prepared separately. Solution No. 1 was prepared as follows. To 55.0 grams of a 75% solution of (3-acrylamidopropyl) trimethyl ammonium chloride (0.20 moles) was added 21.3 grams of deionized water, and 6.0 grams of PEG 200 (molecular weight 200). Then, 0.18 grams ($1.02 \times 10^{-3}$ moles) of ascorbic acid was added to the solution. This mixture was stirred with a magnetic stir bar at about 60 rpm in a bath of water at about 23° C. until the ascorbic acid was dissolved and the mixture cooled to 23° C.

Solution No. 2 was prepared in the following manner. To 55.0 grams of a 75° C. solution of (3-acrylamidopropyl) trimethyl ammonium chloride (0.20 moles) was added 21.3 grams of deionized water, 6.0 grams of PEG 200 (molecular weight 200), 0.37 ml of 30% aqueous hydrogen peroxide and 1.0 ml ($5.42 \times 10^{-3}$ moles) of 3-(trimethoxysilyl)propyl methacrylate. This mixture was stirred with a magnetic stir bar at about 60 rpm in a bath of water at about 23° C. to provide a clear solution cooled to 23° C.

Solution No. 2 was added to Solution No. 1 while stirring with a magnetic stir bar. A thermocouple was used to monitor the temperature and observe the reaction exotherm. No polymerization exotherm was evident so the mixture was placed into a water bath and the temperature was raised from 23° C. to 70° C. over a time period of 35 minutes. An exotherm was evident by a rise in temperature to 73° C. over a period of 1 minute and the solution became highly viscous. The reaction beaker was removed from the water bath after 50 minutes from the addition of Solution No. 2 to Solution No. 1. 152 grams of deionized water was added to reduce the polymer concentration to about 33%.

To 50 grams of the 33% polymer solution was added 2.5 ml of a 0.2% solution of hydrochloric acid. This solution was poured into two weighing dishes (about 24 grams into each dish with 80 cm² area) and the solution was dried for two days in the laboratory hood. The resultant film was very soft and flexible and slightly tacky. The absorbent capacity of the film was tested using the Centrifuge Retention Capacity test described below. The film had an absorbent capacity of 15.3 grams/gram.

Additional monomers that can be incorporated into the composition include, but are not limited to, acrylic acid or

TABLE 1

| Drying Time (minutes) | Fabric Weight (grams) | Weight of Solution Applied (grams) | Weight After Drying (grams) | g/g Absorbent Capacity Based On Weight After Drying | Re-dry Weight (grams) | % Extractable |
|---|---|---|---|---|---|---|
| 5 | .51 | 12.34 | 5.61 | 0.7 | .79 | 86 |
| 7 | .52 | 11.15 | 3.66 | 3.5 | .83 | 77 |
| 9 | .51 | 11.02 | 2.50 | 3.7 | .95 | 62 |
| 11 | .51 | 11.63 | 1.80 | 5.4 | 1.01 | 44 |
| 13 | .54 | 11.64 | 1.66 | 6.0 | 1.07 | 35 |
| 15 | .53 | 12.46 | 1.61 | 5.8 | 1.11 | 31 | acrylamide. The composition may contain from about 15 to 99 percent by weight of a cationic quaternary amine acrylate with the balance made up of other monomers such as acrylic acid or acrylamide. The extent of neutralization of the acrylic acid can range from 5 to 95 mole percent.

In addition, the cationic absorbent binder composition may contain segments of poly(ethylene glycol) that may be grafted to the acrylate copolymer. The amount of poly (ethylene glycol) segments relative to the weight of the polymeric binder composition thereof may range from about 0.1 to about 75 weight percent of poly(ethylene oxide) to the weight of the polymeric binder composition. The cationic quaternary amine acrylate and poly(ethylene)glycol may also be present in the more particular amounts and ranges described previously in the specification.

Any suitable initiator can be used, with redox initiators preferred. The polymerization reaction can be done in aqueous solution, organic solvents, or miscible mixtures of organic solvents and water.

Test Method for Determining Absorbent Capacity

As used herein, the Centrifuge Retention Capacity (CRC) is a measure of the absorbent capacity of the superabsorbent material retained after being subjected to centrifugation under controlled conditions. The CRC can be measured by placing a sample of the material to be tested into a water-permeable bag which will contain the sample while allowing the test solution (0.9 percent NaCl solution) to be freely absorbed by the sample. A heat-sealable tea bag material (available from Dexter Nonwovens of Windsor Locks, Conn., U.S.A., as item #1234T) works well for most applications. The bag is formed by folding a 5-inch by 3-inch sample of the bag material in half and heat sealing two of the open edges to form a 2.5-inch by 3-inch rectangular pouch. The heat seals should be about 0.25 inch inside the edge of the material. After the sample is placed in the pouch, the remaining open edge of the pouch is also heat-sealed. Empty bags are also made to be tested with the sample bags as controls. A sample size is chosen such that the teabag does not restrict the swelling of the material, generally with dimensions smaller than the sealed bag area (about 2-inch by 2.5 inch). Three sample bags are tested for each material.

The sealed bags are submerged in a pan of 0.9% NaCl solution. After wetting, the samples remain in the solution for 60 minutes, at which time they are removed from the solution and temporarily laid on a non-absorbent flat surface.

The wet bags are then placed into the basket of a suitable centrifuge capable of subjecting the samples to a g-force of 350. (A suitable centrifuge is a Heraeus LABOFUGE 400, Heraeus Instruments, part number 75008157, available from Heraeus Infosystems GmbH, Hanau, Germany). The bags are centrifuged at 1600 rpm for 3 minutes (target g-force of 350). The bags are removed and weighed. The amount of fluid absorbed and retained by the material, taking into account the fluid retained by the bag material alone, is the Centrifugal Retention Capacity of the material, expressed as grams of fluid per gram of material.

While the embodiments of the invention disclosed herein are presently preferred, various modifications and improvements can be made without departing from the spirit and scope of the invention. The scope of the invention is indicated by the appended claims; and all changes that fall within the meaning and range of equivalents are intended to be embraced therein.

We claim:

1. An absorbent binder composition combined with water, the absorbent binder composition comprising a water-soluble ionic polymer capable of sufficient moisture-induced crosslinking within about 10 minutes at a temperature of about 120° C. or less, to reach an absorbent capacity of at least one gram per gram using the centrifuge retention capacity test.

2. The absorbent binder composition of claim 1, comprising about 15 to about 99.8% by mass monoethylenically unsaturated polymer units, about 0.1 to about 20% by mass ester units selected from the group consisting of acrylate and methacrylate ester units that include an alkoxysilane functionality, and about 0.1 to about 75% by mass of units selected from the group consisting of polyolefin glycol and polyolefin oxide units.

3. The absorbent binder composition of claim 1, comprising about 25 to about 89.5% by mass monoethylenically unsaturated polymer units, about 0.5 to about 15% by mass ester units selected from the group consisting of acrylate and methacrylate ester units that include an alkoxysilane functionality, and about 10 to about 60% by mass of units selected from the group consisting of polyolefin glycol and polyolefin oxide units.

4. The absorbent binder composition of claim 1, comprising about 30 to about 79% by mass monoethylenically unsaturated polymer units, about 1.0 to about 10% by mass ester units selected from the group consisting of acrylate and methacrylate ester units that include an alkoxysilane functionality, and about 20 to about 50% by mass of units selected from the group consisting of polyolefin glycol and polyolefin oxide units.

5. The absorbent binder composition of claim 1, wherein the water-soluble ionic polymer comprises at least about 15 mole percent ionic polymer units.

6. The absorbent binder composition of claim 1, wherein the ionic polymer has a negative charge.

7. The absorbent binder composition of claim 6, wherein the ionic polymer comprises a carboxyl group-containing monomer.

8. The absorbent binder composition of claim 1, wherein the ionic polymer has a positive charge.

9. The absorbent binder composition of claim 1, wherein the ionic polymer is capable of sufficient moisture-induced crosslinking within about 10 minutes at a temperature of about 120° C. or less, to reach an absorbent capacity of at least 3 grams per gram using the centrifuge retention capacity test.

10. The absorbent binder composition of claim 8, wherein the ionic polymer comprises a quaternary ammonium group-containing monomer.

11. The absorbent binder composition of claim 8, wherein the ionic polymer comprises a reaction product of 1) a monomer selected from the group consisting of acryloyloxyethyl-trialkyl-substituted ammonium salts, acryloyloxypropyl-trialkyl-substituted ammonium salts, acrylamidoethyl-trialkyl-substituted ammonium salts, and acrylamidopropyl-trialkyl-substituted ammonium salts, with 2) a monomer selected from the group consisting of methacryl esters which contain an alkoxysilane group and acryl esters which contain an alkoxysilane group.

12. An absorbent binder composition, comprising:
  a. about 15 to about 99.8% by mass of monoethylenically unsaturated polymer units;
  b. about 0.1 to about 20% by mass polyacrylate ester units that include an alkoxysilane functionality; and
  c. about 0.1 to about 75% by mass polymer units selected from the group consisting of polyolefin glycol units, polyolefin oxide units, and combinations thereof.

13. The absorbent binder composition of claim 12, wherein the monoethylenically unsaturated polymer units and the polyacrylate ester units including an alkoxysilane functionality are copolymerized.

14. The absorbent binder composition of claim 12, wherein at least some of the polymer units selected from the group consisting of polyolefin glycol units, polyolefin oxide units, and combinations thereof are copolymerized with at least some of the polyacrylate ester units.

15. The absorbent binder composition of claim 12, wherein the monoethylenically unsaturated polymer units comprise units selected from the group consisting of carboxyl group-containing units, carboxylic acid anhydride group-containing units, carboxylic acid salt group-containing units, and combinations thereof.

16. The absorbent binder composition of claim 12, wherein the monoethylenically unsaturated polymer units comprise units selected from the group consisting of sulfonic acid group-containing units, sulfonic acid salt group-containing units, and combinations thereof.

17. The absorbent binder composition of claim 12, wherein the monoethylenically unsaturated polymer units comprise amide group-containing units.

18. The absorbent binder composition of claim 12, wherein the polyacrylate ester units comprise acrylate ester units including the alkoxysilane functionality.

19. The absorbent binder composition of claim 12, wherein the polyacrylate ester units comprise methacrylate ester units including the alkoxysilane functionality.

20. The absorbent binder composition of claim 12, wherein the alkoxysilane functionality comprises a trialkoxysilane group having the following structure:

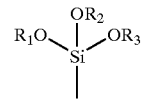

wherein R1, R2 and R3 are alkyl groups independently having from 1 to 6 carbon atoms.

21. The absorbent binder composition of claim 12, wherein component c) comprises a polyolefin glycol including an olefin having about 2 to about 4 carbon atoms.

22. The absorbent binder composition of claim 21, wherein the polyolefin glycol has a weight average molecular weight of about 200 to about 8000.

23. The absorbent binder composition of claim 21, wherein the polyolefin glycol is selected from the group consisting of polyethylene glycol, polypropylene glycol and combinations thereof.

24. The absorbent binder composition of claim 21, wherein component c) comprises a polyolefin oxide including an olefin having about 2 to about 12 carbon atoms.

25. The absorbent binder composition of claim 24, wherein the polyolefin oxide has a weight average molecular weight of about 100,000 to about 600,000.

26. The absorbent binder composition of claim 24, wherein the polyolefin oxide is selected from the group consisting of polyethylene oxide, polypropylene oxide, and combinations thereof.

27. An absorbent article comprising the absorbent binder composition of claim 1.

28. An absorbent article comprising the absorbent binder composition of claim 12.

* * * * *

UNITED STATES PATENT AND TRADEMARK OFFICE
CERTIFICATE OF CORRECTION

PATENT NO. : 6,887,961 B2
DATED : May 3, 2005
INVENTOR(S) : Dave Allen Soerens et al.

It is certified that error appears in the above-identified patent and that said Letters Patent is hereby corrected as shown below:

Title page,
Item [*] Notice, add -- This patent is subject to a Terminal Disclaimer. --; and
Item [63], Foreign Application Priority Data, replace the entire phrase beginning with "Continuation-in-part of application No. 10/206,883..." and ending with "... filed on Dec. 20, 2002." with the following phrase:
-- Continuation-in-part of application No. 10/324,478, filed on Dec. 20, 2002, now Pat. No. 6,849,685, which is a continuation-in-part of application No. 10/206,883, filed on Jul. 26, 2002, now Pat. No. 6,737,491. --

Signed and Sealed this

Twenty-sixth Day of July, 2005

JON W. DUDAS
*Director of the United States Patent and Trademark Office*